United States Patent
Haas et al.

(10) Patent No.: US 9,963,404 B2
(45) Date of Patent: May 8, 2018

(54) METHOD FOR PRODUCING ENVIRONMENTALLY-FRIENDLY PLASTICIZERS

(71) Applicant: Continental Reifen Deutschland GmbH, Hannover (DE)

(72) Inventors: Ewgeni Haas, Hamburg (DE); Carla Recker, Hannover (DE); Thorsten Torbruegge, Langenhagen (DE)

(73) Assignee: Continental Reifen Deutschland GmbH, Hannover (DE)

( * ) Notice: Subject to any disclaimer, the term of this patent is extended or adjusted under 35 U.S.C. 154(b) by 373 days.

(21) Appl. No.: 13/904,784

(22) Filed: May 29, 2013

(65) Prior Publication Data

US 2013/0261356 A1  Oct. 3, 2013

Related U.S. Application Data

(63) Continuation of application No. PCT/EP2011/069925, filed on Nov. 11, 2011.

(30) Foreign Application Priority Data

Dec. 22, 2010  (DE) .................. 10 2010 061 480

(51) Int. Cl.
| | |
|---|---|
| *C07C 4/22* | (2006.01) |
| *C10G 1/10* | (2006.01) |
| *C08J 11/12* | (2006.01) |
| *C10G 1/02* | (2006.01) |
| *B29B 7/74* | (2006.01) |

(52) U.S. Cl.
CPC ............. *C07C 4/22* (2013.01); *B29B 7/7495* (2013.01); *C08J 11/12* (2013.01); *C10G 1/02* (2013.01); *C10G 1/10* (2013.01); *C08J 2317/00* (2013.01); *C08J 2319/00* (2013.01); *C08J 2321/00* (2013.01); *C10G 2300/1003* (2013.01); *Y02W 30/703* (2015.05)

(58) Field of Classification Search
CPC .... C07C 4/22; C10G 1/02; C10G 1/10; C10G 2300/1003; C08J 11/12; C08J 2317/00; C08J 2319/00; C08J 2321/00

USPC .......................................................... 585/241
See application file for complete search history.

(56) References Cited

U.S. PATENT DOCUMENTS

| | | | | |
|---|---|---|---|---|
| 4,322,336 A | * | 3/1982 | Machurat et al. ............ | 524/104 |
| 4,870,112 A | * | 9/1989 | Knipp et al. .................... | 521/70 |
| 5,364,996 A | * | 11/1994 | Castagnoli ................ | C10J 3/46 |
| | | | | 208/407 |
| 5,836,524 A | * | 11/1998 | Wang ........................ | C10B 7/10 |
| | | | | 241/23 |
| 7,335,692 B2 | | 2/2008 | Vasseur et al. | |
| 8,236,875 B2 | | 8/2012 | Recker et al. | |
| 2004/0077908 A1 | * | 4/2004 | Skworcow .......... | B29C 49/0005 |
| | | | | 585/241 |
| 2006/0281956 A1 | | 12/2006 | Bochaver | |
| 2008/0072478 A1 | * | 3/2008 | Cooper .................... | C10G 1/00 |
| | | | | 44/606 |

FOREIGN PATENT DOCUMENTS

| | | |
|---|---|---|
| DE | 101 08 981 A1 | 9/2002 |
| DE | 102 15 679 A1 | 11/2003 |
| DE | 10 2005 040 490 A1 | 2/2007 |

OTHER PUBLICATIONS

Cooper, W. D.; Downing, R. C.; and Gray, J. B., "Alkyl Benzene as a Compressor Lubricant" (1974), International Compressor Engineering Conference, Paper 103, pp. 88-94.*

Benedek et al., 3.1.1.3.3 Plasticizers, Technology of Pressure-Sensitive Adhesives and Products, CRC Press, 2009, pp. 3-28 to 3-29.*

International Search Report dated Feb. 2, 2012 of international application PCT/EP2011/069925 on which this application is based.

* cited by examiner

*Primary Examiner* — Philip Louie

(74) *Attorney, Agent, or Firm* — Walter Ottesen, P.A.

(57) ABSTRACT

A process for producing an environmentally-friendly plasticizer, which is particularly suitable for use in vehicle tires or technical rubber articles. A vulcanized and/or unvulcanized polymer material of a high molecular weight is converted into a low-molecular phase by direct thermal liquefaction. The vulcanized and/or unvulcanized high-molecular-weight polymer material is provided as a polymer powder and/or a granulated polymer and can be obtained from used tires.

8 Claims, No Drawings

METHOD FOR PRODUCING ENVIRONMENTALLY-FRIENDLY PLASTICIZERS

CROSS REFERENCE TO RELATED APPLICATIONS

This application is a continuation application of international patent application PCT/EP2011/069925, filed Nov. 11, 2011, designating the United States and claiming priority from German application 10 2010 061 480.7, filed Dec. 22, 2010, and the entire content of both applications is incorporated herein by reference.

FIELD OF THE INVENTION

The invention relates to a process for producing environmentally friendly plasticizer which is in particular suitable for use in tires or in industrial rubber items.

BACKGROUND OF THE INVENTION

Plasticizers represent, alongside rubber and fillers, another important class of additives in the rubber mixtures used for tires (pneumatic tires, bicycle tires, solid rubber tires) and in industrial rubber items (hoses, drive belts, other belts, printing blankets, membranes, gaskets, air springs, bellows, automobile-interior cladding, synthetic leather). Large amounts of plasticizers are sometimes added to rubber mixtures, in order to reduce the cost of the mixture, to improve the flow properties of the mixture (energy saving during processing, avoidance of energy peaks), to improve filler dispersion, to improve packing and adhesion behavior, and to influence the physical properties of the mixture and of the vulcanizates produced therefrom.

Almost all of the plasticizers used in the rubber industry are generally based on petroleum. For environmental reasons, especially with a view to the current levels of pollutant emissions and current shortages of raw material, petroleum is no longer an acceptable starting material for future production of rubber plasticizers. Alternatives used as plasticizers in rubber mixtures are by way of example vegetable oils, as described for example in DE 101 08 981 A1 and U.S. Pat. No. 7,335,692. The vegetable oils described in those publications can be used as sole plasticizer, but are mostly used in combination with another plasticizer obtained from petroleum. However, the vegetable oils are also subject to limitations on amounts available to the rubber industry.

U.S. Pat. No. 8,236,875 describes, as another alternative, the use of what are known as BTL oils (Biomass-To-Liquid oils). Solid biomasses are starting material for the production of the plasticizers here, which can in turn proceed by various routes. Examples that may be mentioned are flash pyrolysis, with very short residence times in the reactor, direct liquefaction with hydrogenation, where use of (pressurized) hydrogen during the pyrolysis produces stable hydrocarbon products, the process known as the Carbo-V process, which is based on the Fischer-Tropsch process, and direct catalytic liquefaction, in which the pyrolysis proceeds in a sump, with addition of catalyst. Direct liquefaction processes are described in very general terms by way of example in DE 102 15 679 A1 and DE 10 2005 040 490 A1.

A direct liquefaction process for biomass is disclosed in Willner, Marktfruchtreport [Report on commercial agriculture] 2005, Mitteilungen der Landwirtschaftskammer, Landwirtschaftskammer Schleswig-Holstein, Kiel.

However, the problem here is that there are restrictions on the amount of biomass available. If BTL production is used on a larger scale in the future, not only for fuels but also for plasticizer oils, this will therefore lead to land- and utilization-based competition brought about by the increased utilization of agricultural and forestry land. The cost of harvesting, transport, shredding, et cetera also has to be considered.

SUMMARY OF THE INVENTION

It is then an object of the invention to provide a process which can produce environmentally friendly plasticizers and which gives a plasticizer that firstly can reliably provide independence from petroleum as the raw material and energy source, and which secondly does not exhibit the above-mentioned problems posed by BTL oils. A further intention is that the starting materials for the production of the plasticizer be relatively easily available.

The object is achieved via a process for producing plasticizer, characterized in that high-molecular-weight vulcanized and/or high-molecular-weight unvulcanized polymer material is converted to a low-molecular-weight phase via direct thermal liquefaction.

Surprisingly, it has been found that an environmentally friendly plasticizer can be produced from polymer material.

To this end, the high-molecular-weight polymer material is converted via direct thermal liquefaction to a low-molecular-weight phase. After conversion, the low-molecular-weight phase is obtained in a suitable manner known to the person skilled in the art, and can be used as environmentally friendly plasticizer for rubber mixtures. A final result of this is a marked improvement in the ecobalance of the final products, such as tires and industrial rubber items. "Low-molecular-weight phase" means that the plasticizer takes the form of plasticizer oil.

The high-molecular-weight vulcanized and/or high-molecular-weight unvulcanized polymer material preferably involves rubbers, that is, resilient polymers, rubber mixtures (green or vulcanized), thermoplastic elastomers (TPE), mixtures comprising TPE (green or vulcanized), thermoplastics, or thermosets. In particular, rubber mixtures provided for use in tires or in technical rubber items (green mixture), or which had been provided for this purpose (vulcanized mixture, waste), or which previously have been used for this purpose (vulcanized mixture, used waste) can be used for producing the plasticizer. Mixtures of two or more of the abovementioned polymer materials can be used.

Since the polymer materials mentioned generally involve waste materials, by way of example those arising during or after the production of tires or of industrial rubber items (TRG=technical rubber goods), or which take the form of used tires or used TRGs, or which take the form of plastics waste, for example from packaging or the like, an example being lightweight shredder fractions, the process of the invention provides an additional route to the recycling of waste materials of these types. The plasticizer produced via direct thermal liquefaction of polymer material can be used in the same way as a plasticizer used hitherto in the rubber industry. Genuine "recycling" takes place rather than "downcycling", since there is no need to make any compromises in relation to the physical properties of the final finished products.

A reason for this, in particular in the case of filled polymer materials, is that by virtue of the use of the direct thermal liquefaction of polymer material, the resultant plasticizer has no adverse effect on the reinforcing action of the fillers usually present in rubber mixtures. Known pyrolytic processes lead to plasticizers that are used as fuel in energy recycling and which cause a marked loss in the reinforcement potential of the fillers present in the rubber mixture.

In relation to simplified conduct of a process, it has been found advantageous that the polymer material takes the form of polymer powder and/or of granulated polymer. This simplifies introduction of the polymer material into the appropriate reaction apparatus.

The polymer powder and/or the granulated polymer is preferably based on used tires, and in a preferred embodiment comprises natural or synthetic rubber and/or butadiene rubber and/or styrene-butadiene rubber.

These diene rubbers are typically used for producing tires and TRG, and are therefore available in the appropriate waste materials. Furthermore, when the rubbers mentioned are present in the polymer material it is possible to achieve a particularly good yield of plasticizer. Yields found are preferably 90% or more.

The direct thermal liquefaction of polymer material preferably is in essence based on the BTL production process.

Particularly good results are achieved when the direct thermal liquefaction of polymer material takes place at temperatures of from 100 to 500° C., preferably at temperatures of from 150 to 420° C.

Cracking of the high-molecular-weight vulcanized and/or high-molecular-weight unvulcanized polymer material in a bottom phase is also advantageous. In one preferred embodiment, the cracked bottom phase can be the final product.

Cracking is a term used by the person skilled in the art for the cleavage of hydrocarbons of relatively high chain length (high molecular weight) to give hydrocarbons of relatively low chain length (low molecular weight).

In the BTL production process, a distinction is often drawn between single-stage and two-stage processes, where in the case of two-stage processes the production process in essence involves gasification in a first step to produce a synthesis gas and the synthesis of a fuel in a second step.

For the purposes of the process of the invention, it has proven to be advantageous to carry out the cracking in a single stage. The single-stage process delivers a good yield, and at the same time saves an additional step.

The process can moreover be carried out batchwise, that is, stepwise, or continuously, the latter here being the particularly preferred variant, since it minimizes complication on an industrial scale.

Use of at least one feed oil for the conversion of the high-molecular-weight vulcanized and/or high-molecular-weight unvulcanized polymer material to a low-molecular-weight phase has also proven advantageous. This is true not only for the batchwise process but also for the continuous process, and in the continuous process here the feed oil is in essence used for the startup of the process.

When a feed oil is used, it is first heated to a temperature suitable for the appropriate oil, and then the polymer material to be cracked is added thereto. A suitable temperature for the feed oil should generally be a temperature at which the feed oil does not yet undergo full onset of decomposition, this being apparent via the absence of a blank stream.

In a preferred embodiment, the feed oil is one selected from the group consisting of mineral oil, lubricants made of long and short-chain hydrocarbons, vegetable oils and liquid polymer with an average molar mass $M_W$ of from 150 to 5000 g/mol. However, it is also possible that the feed oil is a BTL oil or an oil which has been produced by a process as disclosed herein, or a mixture of these oils and/or of the abovementioned oils.

Vegetable oils are mixtures of various acylglycerols, and also comprise other ancillary substances, such as free fatty acids, phospholipids, dyes, sterols, ethereal oils, vitamins, etc. In one preferred embodiment, the vegetable oils involve rapeseed oil and/or involve sunflower oil.

If mineral oil is used, this is preferably one selected from the group consisting of DAE (Distillate Aromatic Extracts) and/or RAE (Residual Aromatic Extract) and/or TDAE (Treated Distillate Aromatic Extracts) and/or MES (Mild Extracted Solvents) and/or naphthenic oils, particular preference being given to TDAE.

DESCRIPTION OF THE PREFERRED EMBODIMENTS OF THE INVENTION

An inventive example will now be used for further explanation of this disclosure. In this connection, Table 1 lists the features of the polymer materials used, and of the plasticizer produced by using the process disclosed herein.

Inventive Example

The polymer material used comprises a rubber powder obtained from a vulcanized mixture for the tread of a truck tire. The rubber powder comprises, as rubber component, high proportions of a natural polyisoprene (NR), low proportions of polybutadiene rubber (BR), and sometimes only traces of styrene-butadiene rubber (SBR). The phr data (parts by 100 parts of rubber by weight) used in Table 1 here are the customary qualitative data used for mixture formulations in the rubber industry. The amount added in parts by weight of individual substances here is always based on 100 parts by weight of the entire composition of all of the rubbers present in the mixture. The inventive example relates to laboratory-scale experiments, and for industrial applications the corresponding parameters have to be adapted appropriately, in particular depending on the size of the corresponding reactor.

The plasticizer oil was produced by the process disclosed herein. TDAE oil was used as feed oil. 302.42 g of TDAE oil (VIVATEC 500, Hansen-Rosenthal KG, Hamburg) were heated to 300° C. in a reaction apparatus of volume 1 l. The heating phase takes 80 minutes to reach the desired bottom temperature of 300° C. This is then maintained for 22 minutes in order to record what is known as the blank value. The blank value is a product mass flow rate resulting from the cracking of the feed oil. This flow rate is also present subsequently during the addition of the polymer material, and the total condensate mass flow rate during the experiment is therefore composed of the blank value and of the mass flow rate resulting from the addition of the polymer material. Once the heating time has expired, the introduction of the polymer material is begun. Another factor to be considered here is a change of fraction, to permit better evaluation of the effect of the polymer material on the condensate produced. During the controlled and continuous introduction of the polymer material, the torque of the stirrer in the reaction apparatus is observed, in order to ensure that the viscosity of the bottom product does not rise excessively. In the event of temporary viscosity rises, the introduction of the polymer material can be briefly interrupted in a controlled manner. In the present inventive example, 604.31 g of polymer material are added at a rate of 111.57 g/h within a period of 325 minutes. The temperature is maintained at 300° C. during the entire direct thermal liquefaction process.

Table 1 shows that there is no residual content of high-molecular-weight polymer material.

The following test methods were used, insofar as these are not stated directly in the Table:

Acetone extract (=entirety of all of the substances extractable from the vulcanized rubber mixture, for example antioxidants, plasticizers, et cetera) in accordance with DIN ISO 308

Carbon black content, using TGA in accordance with DIN 51006

Residue on ignition at 550° C. in accordance with DIN 53568, DIN 12904, DIN 12491

Sulfur content in accordance with ASTM D2622

Glass transition temperature Tg in accordance with ISO DIS 28343

Content of polycyclic aromatics (PAH value) in accordance with IP 346

Nitrogen content based on ASTM 147

Zn, Cu, Fe content based on ASTM D7260

TABLE 1

| Test method | Unit | Powder 1 | Plasticizer oil |
|---|---|---|---|
| Acetone extract | % | 6.4 | — |
| Carbon black content | % by wt. | 28.7 | 15.2 |
| Residue on ignition | % | 6 | 3.2 |
| Sulfur content | % | 1.22 | 1.11 |
| Tg | ° C. | −62 | −17 |
| NR | phr | 83 | — |
| BR | phr | 17 | — |
| SBR | phr | traces | — |
| PAH | % | — | 0.12 |
| Nitrogen content | % | — | 0.23 |
| Zn | % | 1.06 | 0.58 |
| Cu | mg/kg | 1.4 | 3.5 |
| Fe | mg/kg | 24.9 | 7.6 |
| Viscosity @ RT | | n.a. | paste-like |

It is understood that the foregoing description is that of the preferred embodiments of the invention and that various changes and modifications may be made thereto without departing from the spirit and scope of the invention as defined in the appended claims.

What is claimed is:

1. A process for producing plasticizer comprising:
providing a feed oil for a conversion of a polymer material to a plasticizer,
heating the feed oil to a temperature of from 150 to 300° C. and adding the polymer material to the heated feed oil,
converting the polymer material to the plasticizer via direct thermal liquefaction in a single stage reactor,
obtaining the plasticizer as a final product from the single stage reactor, and
performing the direct thermal liquefaction at the same temperature to which the feed oil has been heated,
wherein the polymer material is powder or granulated polymer from rubber tires, and
wherein the feed oil is vegetable oil comprising rapeseed oil and/or sunflower oil, or Treated Distillate Aromatic Extracts (TDAE).

2. The process as claimed in claim 1, wherein the polymer material comprises a rubber selected from the group consisting of natural rubber, synthetic rubber, butadiene rubber, styrene-butadiene rubber, and mixtures thereof.

3. The process as claimed in claim 1, further comprising performing the direct thermal liquefaction in a sump phase.

4. The process of claim 1, wherein the feed oil consists essentially of rapeseed oil and/or sunflower oil.

5. The process of claim 2, wherein the yield of plasticizer is 90% or more.

6. The process of claim 1, wherein the feed oil does not undergo full decomposition and does not produce a blank stream at the temperature of from 150 to 300° C.

7. The process of claim 1, wherein converting the polymer material to the plasticizer via direct thermal liquefaction in a single stage reactor occurs at a constant temperature of 300° C. throughout the process.

8. A process for producing plasticizer comprising:
providing a feed oil for a conversion of a polymer material to a plasticizer,
heating the feed oil to a temperature of 300° C. and adding the polymer material to the heated feed oil,
converting the polymer material to the plasticizer via direct thermal liquefaction in a single stage reactor,
obtaining the plasticizer as a final product from the single stage reactor, and
performing the direct thermal liquefaction at the same temperature to which the feed oil has been heated,
wherein the polymer material used is powder or granulated polymer from rubber tires, and
wherein the feed oil is Treated Distillate Aromatic Extracts (TDAE).

* * * * *